United States Patent [19]

Laurent

[11] Patent Number: 5,612,379
[45] Date of Patent: Mar. 18, 1997

[54] MODAFINIL FOR THE TREATMENT OF SLEEP APNEAS AND VENTILATORY DISORDERS OF CENTRAL ORIGIN

[75] Inventor: Philippe Laurent, Oullins, France

[73] Assignee: Laboratoire L. Lafon, Maisons Alfort, France

[21] Appl. No.: 564,286

[22] PCT Filed: Jun. 14, 1994

[86] PCT No.: PCT/FR94/00711

§ 371 Date: Apr. 30, 1996

§ 102(e) Date: Apr. 30, 1996

[87] PCT Pub. No.: WO95/00132

PCT Pub. Date: Jan. 5, 1995

[30] Foreign Application Priority Data

Jun. 22, 1993 [FR] France .................................. 93 07555

[51] Int. Cl.$^6$ .................................................. A61K 31/165
[52] U.S. Cl. ............................................................ 514/618
[58] Field of Search ................................................ 514/618

[56] References Cited

U.S. PATENT DOCUMENTS

| | | | |
|---|---|---|---|
| 4,177,290 | 12/1979 | Lafon | 424/324 |
| 5,180,745 | 1/1993 | Lafon | 514/618 |
| 5,281,607 | 1/1994 | Stone et al. | 514/280 |
| 5,391,576 | 2/1995 | Lafon | 514/618 |

FOREIGN PATENT DOCUMENTS

| | | |
|---|---|---|
| 0462004 | 12/1991 | European Pat. Off. . |
| 2385693 | 10/1978 | France . |
| 2684875 | 7/1993 | France . |

*Primary Examiner*—Raymond Henley, III
*Attorney, Agent, or Firm*—Jacobson, Price, Holman & Stern, PLLC

[57] ABSTRACT

The present invention relates to the utilization of modafinil for the treatment of ventilation disorders of central origin such as sleep apnea.

3 Claims, No Drawings

MODAFINIL FOR THE TREATMENT OF SLEEP APNEAS AND VENTILATORY DISORDERS OF CENTRAL ORIGIN

The present invention relates to a new use in therapeutics of modafinil.

Modafinil or benzhydrylsulphinyl acetamide is a compound of formula:

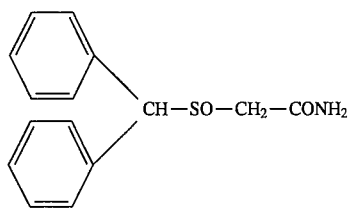

This compound and its therapeutic application as an agent which is active with respect to the central nervous system have been described in Patent Application FR-A-2,385,693. This application describes pharmacological properties showing waking and antidepressant pharmacological effects. Very favourable results are mentioned for the treatment of asthenias in elderly people. The product is furthermore described as useful in the treatment of tardive dyskinesias of neuroleptics. Application FR-A-2,663,225 describes therapeutic properties which are useful in the treatment of neurodegenerative diseases of the dopaminergic pathways of the central nervous system, such as Parkinson's disease. Moreover, French Patent Application 91 15 534 describes properties which are useful in the treatment of sequel of cerebral ischaemic accidents.

It has now been discovered that modafinil has a beneficial effect with respect to apneas occurring during sleep apnea syndromes.

The subject of the present invention is consequently the use of modafinil for the manufacture of a medicament having a beneficial effect on the occurrence of the apneas which characterize sleep apnea syndromes, and more generally ventilatory disorders of central origin.

The anti-apnea medicament containing modafinil can be presented in particular in a form suitable for oral administration. Generally, the dose administered can be from 1 mg/kg to 100 mg/kg.

It will be recalled that an apnea is defined as an interruption of the nasobuccal airflow exceeding a duration arbitrarily set at 10 seconds (Guilleminault C., Tilkian A., Dement W C.: *Ann. Rev. Med.,* 1976, 27: 465–484). Three types of apnea are to be distinguished: apneas of central origin, apneas by obstruction of the airways, and apneas, known as mixed apneas, combining the two central and obstructive causes. Sleep apnea syndromes are conventionally defined by an apnea number greater than 5 apneas per hour of sleep. More recently, the syndromes are defined by an apnea and hypopnea number greater than 10 events per hour of sleep.

The result of a clinical trial demonstrating the anti-apnea effects of modafinil in man will be given below.

6 subjects, of both sexes, monitored in a specialist hospital department and suffering from sleep apnea syndrome of central and mixed origin were included in a single-blind pilot clinical trial comparing the effect of modafinil with the usual treatments such as CIPAP. The patients were diagnosed by a polysomnographic recording method comprising the identification of the sleep stages and the measurement of the duration of each stage, the detection of apneas and the measurement of the consequences of these apneas on the arterial gasometric parameters, the heart rate and the arterial pressure. Identification of the sleep stages was carried out using electroencephalographic (EEG), electromyographic (EMG) and electro-oculographic (EOG) recordings. Ventilatory activity was determined using thermistors. Oxygen saturation of haemoglobin was measured by transcutaneous oximetric measurement. Finally, the other gasometric parameters were measured using an automatic gas analyser of Corning type. Clinical signs such as diurnal somnolence and the quality of nocturnal sleep were assessed using a clinical assessment scale and a sleep diary filled in by the patient and the clinical investigator. Modafinil was administered during the day, preferably in the morning and at the beginning of the afternoon.

The results unexpectedly report an effect on the number of nocturnal apneas occurring during sleep and hypopnea. This number significantly decreases in 4 subjects out of 6 after 1 month of treatment and, in one subject out of 6, the apneas disappear completely from the recordings after treatment. The improvement relating to the number of apneas occurring during sleep seems to persist for several days after interruption of the treatment. The modafinil doses administered per day were from 200 mg to 600 mg.

By way of example, the results obtained with one patient are presented in Table I, which compares the results relating to the apneas before and during the treatment with modafinil.

The treatment with modafinil contributed to improving diurnal somnolence and the quality of nocturnal sleep.

The clinical results observed in man make it possible to envisage the application of the medicament in the treatment of sleep apneas and more generally to ventilatory disorders of central origin.

TABLE I

|  | Before treatment | During the treatment |
|---|---|---|
| RESULTS RELATING TO THE APNEAS | | |
| TOTAL NUMBER OF APNEAS | 368 | 3 |
| Number of central apneas | 269 | 2 |
| Number of peripheral apneas | 59 | 1 |
| Number of mixed apneas | 40 | 0 |
| TOTAL DURATION OF THE APNEAS | 7432 sec | 35 sec |
| Total duration of the central apneas | 5546 sec | 23 sec |
| Total duration of the peripheral apneas | 988 sec | 12 sec |
| Total duration of the mixed apneas | 898 sec | 0 sec |
| OVERALL DISTRIBUTION OF THE APNEAS | | |
| APNEAS OF LESS THAN 10 SECONDS | | |
| Number | 2 | 0 |
| Total duration | 18 sec | 0 sec |
| Mean duration | 9 sec | 0 sec |
| Total duration/duration of sleep | 0.06% | 0% |
| APNEAS EQUAL TO OR GREATER THAN 10 SECONDS | | |
| Number | 366 | 3 |
| Total duration | 7414 sec | 35 sec |
| Mean duration | 20 sec | 12 sec |
| Total duration/duration of sleep | 26.23% | 0.15% |
| APNEA NUMBER | 46.62 | 0.45 |
| APNEA RATE | 26.3% | 0.15% |

I claim:

1. Process for the treatment of ventilatory disorders of central origin comprising the administration to a patient of an effective amount of modafinil.

2. Process according to claim 1 comprising the oral administration of 1 to 100 mg of modafinil par kg of body weight.

3. Process as claimed in claim 1 for reducing the number of apneas occurring during sleep apnea syndromes.

* * * * *